US009280746B2

(12) United States Patent
Lindhiem (10) Patent No.: US 9,280,746 B2
(45) Date of Patent: Mar. 8, 2016

(54) POSTERIOR PROBABILITY OF DIAGNOSIS INDEX

(71) Applicant: University of Pittsburgh—Of the Commonwealth System of Higher Education, Pittsburgh, PA (US)

(72) Inventor: Oliver James Lindhiem, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 244 days.

(21) Appl. No.: 13/944,802

(22) Filed: Jul. 17, 2013

(65) Prior Publication Data
US 2014/0025623 A1  Jan. 23, 2014

Related U.S. Application Data

(60) Provisional application No. 61/673,020, filed on Jul. 18, 2012.

(51) Int. Cl.
| | |
|---|---|
| *G06F 9/44* | (2006.01) |
| *G06F 7/02* | (2006.01) |
| *G06F 7/06* | (2006.01) |
| *G06N 5/04* | (2006.01) |
| *G06F 19/00* | (2011.01) |

(52) U.S. Cl.
CPC .............. *G06N 5/048* (2013.01); *G06F 19/345* (2013.01)

(58) Field of Classification Search
None
See application file for complete search history.

(56) References Cited

U.S. PATENT DOCUMENTS

2003/0232314 A1* 12/2003 Stout et al. ................. 434/322

OTHER PUBLICATIONS

Heckerman "A Tutorial on Learning with Bayesian Networks", MSR-TR-95-06, 1995, 58 pages.*
Glickman et al. "A non-parametric Bayesian diagnostic for detecting differential item functioning in IRT models", Health Serv Outcomes Res Method, 2009, 17 pages.*
Glas et al. "A Bayesian Approach to Person Fit Analysis in Item Response Theory Models", Applied Psychological Measurement, vol. 27 No. 3, May 2003, 217-233.*
Achenbach, T. M. "Empirically based assessment and taxonomy: Applications to clinical research." Psychological Assessment, 7, 261-274 (1995).
Aggen, S. H., Neale, M. C., & Kendler, K. S. "DSM criteria for major depression: Evaluating symptom patterns using latent-trait item response models." Psychological Medicine: A Journal of Research in Psychiatry and the Allied Sciences, 35, 475-487 (2005).
Bedi, R. P., Maraun, M. D., & Chrisjohn, R. D. "A multisample item response theory analysis of the Beck Depression Inventory-1A." Canadian Journal of Behavioural Science/Revue canadienne des sciences du comportement, 33, 176-187 (2001).

(Continued)

*Primary Examiner* — Li-Wu Chang
(74) *Attorney, Agent, or Firm* — Klarquist Sparkman LLP (57) ABSTRACT

The likelihood of a disorder can be determined using a variety of techniques. One or more exhibited symptoms may be obtained for a patient. The likelihood that each symptom will be exhibited for the disorder can be computed, and a posterior probability of the disorder given the exhibited symptoms can be computed from the likelihood of the symptoms. Based on the resulting posterior probability of the disorder, a more accurate determination can be made of whether the patient is suffering from the disorder.

14 Claims, 7 Drawing Sheets

(56) References Cited

OTHER PUBLICATIONS

Bock, R. D., & Mislevy, R. J. "Adaptive EAP estimation of ability in a microcomputer environment." Applied Psychological Measurement, 6, 431-444 (1982).

Borsboom, D., Mellenbergh, G. J., & van Heerden, J. "The theoretical status of latent variables." Psychological Review, 110, 203-219 (2003).

Bruchmüller, K., Margraf, J., & Schneider, S. "Is ADHD diagnosed in accord with diagnostic criteria? Overdiagnosis and influence of client gender on diagnosis. Journal of Consulting and Clinical Psychology," 80, 128-138 (2012).

Burns, G. L., Walsh, J. A., Owen, S. M., & Snell, J. "Internal validity of attention deficit hyperactivity disorder, oppositional defiant disorder, and overt conduct disorder symptoms in young children: Implications from teacher ratings for a dimensional approach to symptom validity." Journal of Clinical Child Psychology, 26, 266-275 (1997).

Burns, G. L., Walsh, J. A., Patterson, D. R., Holte, C. S., Sommers-Flanagan, R., & Parker, C. M. "Internal validity of the disruptive behavior disorder symptoms: Implications from parent ratings for a dimensional approach to symptom validity." Journal of Abnormal Child Psychology, 25, 307-319 (1997).

Cole, D. A., Cai, L., Martin, N. C., Findling, R. L., Youngstrom, E. A., Garber, J., Forehand, R. "Structure and measurement of depression in youths: Applying item response theory to clinical data." Psychological Assessment, 23, 819-833 (2011).

Edens, J. F., Marcus, D. K., Lilienfeld, S. O., & Poythress, N. G., Jr. "Psychopathic, not psychopath: Taxometric evidence for the dimensional structure of psychopathy." Journal of Abnormal Psychology, 115, 131-144 (2006).

Frazier, T. W., Youngstrom, E. A., & Naugle, R. I. "The latent structure of attention-deficit/hyperactivity disorder in a clinic-referred sample." Neuropsychology, 21, 45-64 (2007).

Furukawa, T. A., Andrews, G., & Goldberg, D. P. "Stratum-specific likelihood ratios of the General Health Questionnaire in the community: Help-seeking and physical co-morbidity affect the test characteristics." Psychological Medicine, 32, 743-748 (2002).

Gomez, R., Burns, G. L., & Walsh, J. A. "Parent ratings of the oppositional defiant disorder symptoms: Item response theory analyses of cross-national and cross-racial invariance." Journal of Psychopathology and Behavioral Assessment, 30, 10-19 (2008).

Hunsley, J., & Mash, E. J. "Introduction to the special section on developing guidelines for the evidence-based assessment (EBA) of adult disorders." Psychological Assessment, 17, 251-255 (2005).

Jensen, A. L., & Weisz, J. R. "Assessing match and mismatch between practitioner-generated and standardized interview-generated diagnoses for clinic-referred children and adolescents." Journal of Consulting and Clinical Psychology, 70, 158-168 (2002).

Jensen-Doss, A., & Weisz, J. R. "Diagnostic agreement predicts treatment process and outcomes in youth mental health clinics." Journal of Consulting and Clinical Psychology, 76, 711-722 (2008).

Lindhiem, O., Kolko, D. J., & Yu, L. "Quantifying Diagnostic Uncertainty Using Item Response Theory: The Posterior Probability of Diagnosis Index." Psychological Assessment. Advance online publication (2013).

Mash, E. J., & Hunsley, J. "Evidence-based assessment of child and adolescent disorders: Issues and challenges." Journal of Clinical Child & Adolescent Psychology, 34, 362-379 (2005).

McMahon, R. J., & Frick, P. J. "Evidence-based assessment of conduct problems in children and adolescents." Journal of Clinical Child & Adolescent Psychology, 34, 477-505 (2005).

Meehl, P. E., & Rosen, A. "Antecedent probability and the efficiency of psychometric signs, patterns, or cutting scores." Psychological Bulletin, 52, 194-216 (1955).

Miller, L. S., Bergstrom, D. A., Cross, H. J., & Grube, J. W. "Opinions and use of the DSM system by practicing psychologists." Professional Psychology, 12, 385-390 (1981).

Mokros, A., Schilling, F., Eher, R., & Nitschke, J. "The Severe Sexual Sadism Scale: Cross-validation and scale properties." Psychological Assessment, 24, 764-769 (2012).

Mossman, D. "The meaning of malingering data: Further applications of Bayes' theorem." Behavioral Sciences and the Law, 18, 761-779 (2000).

Orlando, M., & Thissen, D. "Likelihood-based item-fit indices for dichotomous item response theory models." Applied Psychological Measurement, 24, 50-64 (2000).

Orlando, M., & Thissen, D. "Further investigation of the performance of S-X2: An item fit index for use with dichotomous item response theory models." Applied Psychological Measurement, 27, 289-298 (2003).

Peirce, J. C., & Cornell, R. G. "Integrating stratum-specific likelihood ratios with the analysis of ROC curves." Medical Decision Making, 13, 141-151 (1993).

Pelham, W. E., Fabiano, G. A., & Massetti, G. M. "Evidence-based assessment of attention deficit hyperactivity disorder in children and adolescents." Journal of Clinical Child & Adolescent Psychology, 34, 449-476 (2005).

Reise, S. P., & Waller, N. G. "Item response theory and clinical measurement." Annual Review of Clinical Psychology, 5, 27-48 (2009).

Ruscio, A. M., Ruscio, J., & Keane, T. M. "The latent structure of posttraumatic stress disorder: A taxometric investigation of reactions to extreme stress." Journal of Abnormal Psychology, 111, 290-301 (2002).

Ruscio, J., & Ruscio, A. M. "A conceptual and methodological checklist for conducting a taxometric investigation." Behavior Therapy, 35, 403-447 (2004).

Widiger, T. A., & Clark, L. A. "Toward DSM-V and the classification of psychopathology." Psychological Bulletin, 126, 946-963 (2000).

Wikipedia.com, "Diagnostic and Statistical Manual of Mental Disorders," <http://en.wikipedia.org/wiki/Diagnostic_and_Statistical_Manual_of_Mental_Disorders>, 8 pages (accessed Jul. 17, 2013).

Wolraich, M. L., Hannah, J. N., Baumgaertel, A., & Feurer, I. D. "Examination of DSM-IV critieria for attention deficit/hyperactivity disorder in a county-wide sample." Journal of Developmental & Behavioral Pediatrics, 19, 162-168 (1998).

Wolraich, M. L., Lambert, W., Doffing, M. A., Bickman, L., Simmons, T., & Worley, K. "Psychometric properties of the Vanderbilt ADHD diagnostic parent rating scale in a referred population." Journal of Pediatric Psychology, 28, 559-568 (2003).

\* cited by examiner

FIG. 6

POSTERIOR PROBABILITY OF DIAGNOSIS INDEX

CROSS-REFERENCE TO RELATED APPLICATION

This application claims the benefit of U.S. Provisional Application No. 61/673,020, which was filed on Jul. 18, 2012 and is incorporated herein by reference in its entirety.

ACKNOWLEDGMENT OF GOVERNMENT SUPPORT

This invention was made with government support under Grant No. MH093508 awarded by the National Institutes of Health. The government has certain rights in the invention.

BACKGROUND

It is an important social goal to be able to accurately diagnose and treat mental disorders. However, for many of these disorders, tests such as x-rays, blood tests and tests for biomarkers are not helpful for their diagnosis. Therefore, clinicians must rely on other approaches to diagnose a disorder.

Clinicians use various approaches to assist them in the diagnosis of a disorder. However, these approaches have a number of limitations. For example, some solutions count the number of symptoms exhibited by a patient in order to determine whether the patient is suffering from a disorder. However, merely counting a number of symptoms does not take into account differences between the symptoms or different combinations of symptoms, and does not take into account differences within a symptom, such as a range of severities.

In addition, these solutions require the symptom count to exceed a threshold for the diagnosis of the disorder. Thus, as long as a patient exhibits a certain number of symptoms, no matter what those symptoms are, the patient may be diagnosed with the disorder. Further, if the symptom count is at or near this threshold, these solutions do not provide any further information to help the clinician with their diagnosis, leading to inconsistent diagnoses across clinicians.

Therefore, there exists ample opportunity for the improvement in the accuracy of the diagnosis of disorders.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Techniques and tools are described for determining the posterior probability of a disorder. For example, exhibited symptoms can be obtained for a patient. The likelihood that each symptom will be exhibited for the disorder can be computed, and a posterior probability of the disorder given the exhibited symptoms can be computed from the likelihood of the symptoms. Based on the resulting posterior probability of the disorder, a clinician can make a more accurate determination of whether the patient is suffering from the disorder.

For example, a method can be provided for diagnosing a disorder. The method can include obtaining vectors for a set of symptoms of a disorder; receiving indications of symptoms from the set of symptoms; computing probabilities of the indications of symptoms using the vectors, where the probabilities are scaled by theta value; computing a posterior probability distribution of the disorder based on the computed probabilities of the indications of symptoms; and computing a posterior probability of diagnosis index for each theta value from the posterior probability distribution.

The method can be implemented by one or more computer servers (e.g., as part of a server environment or cloud computing environment). The method can provide diagnostic services to one or more client devices. For example, the indications of symptoms can be received from a client device and the posterior probability of diagnosis index can be sent to the client device.

As another example, systems comprising processing units and memory can be provided for performing operations described herein. For example, a system can be provided for diagnosing a disorder (e.g., comprising computer-readable storage media storing computer-executable instructions for causing the system to perform operations for diagnosing a disorder).

As described herein, a variety of other features and advantages can be incorporated into the technologies as desired.

DETAILED DESCRIPTION

Example 1

Exemplary Overview

The following description is directed to techniques and solutions for diagnosing a disorder. For example, indications of symptoms exhibited by a patient can be obtained from a set of symptoms for a disorder. Based on the indications of symptoms, a posterior probability of diagnosis index (PPOD Index) can be computed for the disorder. The PPOD Index can assist clinicians to more accurately diagnose a disorder for a patient. The PPOD Index can also be referred to as a likelihood of diagnosis index (LODI).

The examples described herein can be used to supplement existing approaches to the diagnosis of a disorder by adding another tool that a clinician may use to assist them in the diagnosis of a disorder. Clinicians may use the examples herein in conjunction with existing approaches to the diagnosis of a disorder to arrive at more accurate diagnoses of a disorder. The techniques described herein can also be used separately or independently of existing approaches.

The techniques described herein can be applied to different types of disorders. In some embodiments, the techniques are applied to diagnosis of a mental disorder. However, a disorder is not limited to those disorders that are mental in nature and may refer to any disorder for which a symptom count is used, at least in part, in the determination of the disorder (e.g., medical disorders that use a symptom count).

In any of the examples herein, a clinician may refer to any individual that provides mental diagnosis and/or treatment. Clinicians includes, but are not limited to, physicians, psychiatrists, psychologists, diagnosticians, counselors, social workers, nurses and other health and mental health professionals. Clinicians may also include those professionals that do not directly provide, but assist with, mental diagnosis and treatment. Examples, include statisticians, researchers and public health officials. In the examples described herein, the techniques are applied by a clinician. However, the techniques are not limited to application by a clinician as the techniques can be utilized by anyone.

Example 2

Diagnostic and Statistical Manual of Mental Disorders (DSM)

One traditional approach to the diagnosis of a disorder has been for a clinician to use the Diagnostic and Statistical Manual of Mental Disorders (DSM), published by the American Psychiatric Association, to assist them in making diagnoses for their patients. The DSM contains a list of all recognized mental disorders and exhibited symptoms associated with each disorder. For each disorder, the DSM provides a count of symptoms that must be present to diagnose a patient as suffering from the disorder. However, this approach has a number of disadvantages.

One disadvantage is that clinicians must rely on a symptom count for their diagnosis. Because a DSM diagnosis relies on a symptom count instead of examining which symptoms are being exhibited by the patient, the importance of specific symptoms being exhibited is not factored into the analysis of the disorder.

Figure 1:
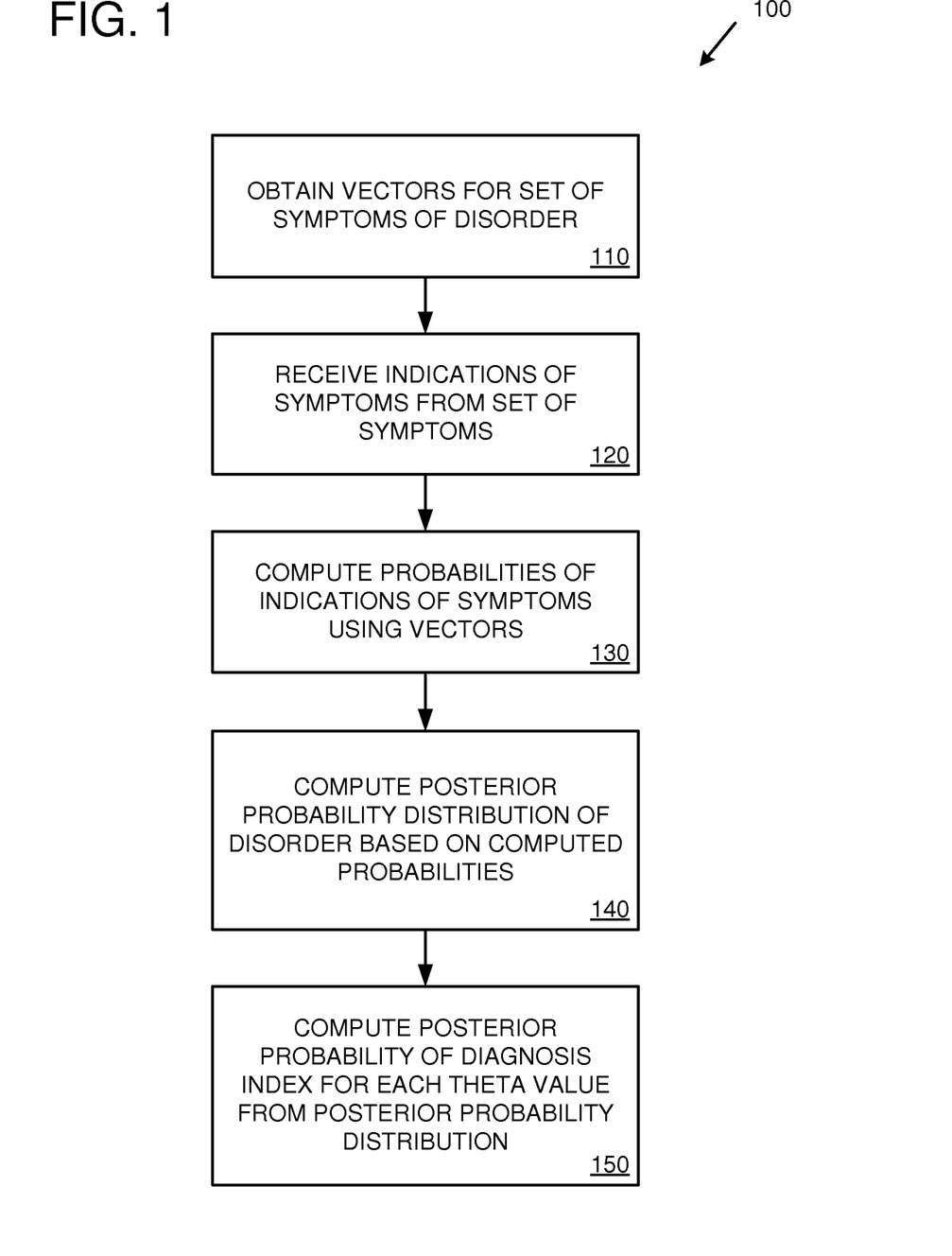
FIG. 1 is a flowchart of an exemplary method for diagnosing a disorder.

Another disadvantage is that the DSM does not provide a clinician a confidence level for their diagnosis. Two patients may exhibit completely different symptoms and may be diagnosed with the same disorder, even though the clinician is more confident that one patient has the disorder than the other patient. The issue is particularly problematic when the clinician is "on the fence" about a diagnosis. For example, if a total of four out of eight symptoms are required to be exhibited in order to make the determination that the patient is suffering from the disorder, any four symptom may be exhibited to determine the presence of the disorder. FIG. 1 depicts eight symptoms 110, 112, 114, 116, 118, 120, 122 associated with a disorder 130. In this example, the symptoms do not need to be consistent throughout the patient population suffering from the disorder. For example, symptoms 110, 114, 118, 122 may be exhibited by one patient and symptoms 112, 116, 120, 124 may be exhibited by a different patient. In this example, both patients would be diagnosed with the disorder.

Another disadvantage is that the symptoms in the DSM are also not weighted. Thus, one symptom is no more determinative of the disorder than another symptom. The DSM does not take into account the probabilities of the symptoms occurring in a disorder, and thus has limitations as a tool in diagnosing disorders.

Example 3

Item Response Theory (IRT)

Item Response Theory (IRT) refers to a class of techniques of modeling the probability of choosing response categories as a function of a latent trait of interest. The latent trait is scaled along a dimension θ, which has a mean of 0 and a standard deviation of 1. A person's responses to a set of items are used to estimate the person's severity level on a particular latent trait. More specifically, IRT uses each person's responses (in this case, symptom endorsements) in conjunction with estimated item parameters to estimate the person's θ level.

The relationship between the probability of choosing a certain response category (e.g., yes or no) for a specific item and the underlying severity level can be described by a monotonically increasing function (i.e., a sigmoid function) called the item characteristic function (ICF). An ICF can be transformed into an item information curve, indicating the amount of information a single item contains at all points along a severity (θ) scale. The amount of information provided by an item may vary depending on the level of a respondent's severity of a disorder (θ).

The most basic unidimensional IRT model is a one-parameter logistic model (also known as the Rasch model) for which each item has a severity or threshold parameter β. This threshold parameter is defined as the latent trait level at which a respondent has a 0.50 chance of endorsing the item. As a result, respondents may differ in the consistency of their response pattern. Two-parameter logistic (2PL) IRT models also have a discrimination parameter a. The discrimination parameter affects the estimate of each patient's latent trait estimate θ. Items with higher discrimination parameters are "weighted" more heavily than items with lower discrimination parameters. For diagnostics, this takes into account the fact that not all items are equally good at discriminating between those who have the disorder and those who do not. Increasingly, IRT is being applied to clinical measurement, including tools such as the Beck Depression Inventory. IRT has already been applied to DSM diagnostic criteria for depression in both adults and youth. Such applications of IRT have led to insights about the discriminability of particular depression symptoms and the reduction in measurement error.

Example 4

Posterior Probability of Diagnosis (PPOD) Index

The posterior probability of a diagnosis is, for example, a measurement of the likelihood of the occurrence of a disorder given the probability of its symptoms. Given a response pattern D (i.e., indications of symptoms) and a patient's IRT trait level θ, a simple Bayesian analysis can be performed to compute the posterior probability p(θ|D) (i.e., the likelihood that the patient meets or exceeds a threshold) using the following equation:

$$p(\theta | D) = \frac{p(D | \theta)p(\theta)}{p(D)} \qquad \text{(Equation 1)}$$

where p(D|θ) is the likelihood of the response pattern given a patient's IRT trait level, p(θ) is the probability of the patient's IRT trait level, and p(D) is the probability of the response pattern.

In any of the examples herein, a patient's IRT trait level is used for the θ value. However, IRT need not be used. For example, any statistical model used to obtain a probability of symptoms and a likelihood of symptoms given a disorder may be used.

In any of the examples herein, the threshold may be a threshold determined by the DSM. For example, if a disorder requires four symptoms, the θ equivalent to four symptoms may be used as the threshold. However, the threshold is not limited to a threshold determined by the DSM. For example, a constant percentage, e.g., 50%, may be used. Alternatively, the θ equivalent of another approach used to correlate symptoms to disorders may also be used.

Example 5

Example Method of Diagnosing a Disorder

FIG. 1 is a flowchart of an exemplary method for diagnosing a disorder.

At 110, vectors are obtained for a set of symptoms associated with a disorder. In any of the examples herein, the vectors may be calculated or may be obtained from a data file or another data source (e.g., as pre-computed vectors for the disorder). The vectors may be calculated from a data set or may be unstructured data. Further description of obtaining the vectors will be provided below.

The set of symptoms of a disorder are those symptoms that are associated with a disorder. The symptoms may be obtained, for example, from the DSM. However, the symptoms of the disorder are not limited to those in the DSM and may be any symptoms that are associated with the disorder (e.g., that show some causal link with the disorder). For example, according to the DSM, oppositional defiant disorder (ODD) is associated with a set of eight symptoms: argues with adults, loses temper, actively defies or refuses to go along with adults' requests or rules, deliberately annoys people, blames others for his or her mistakes or misbehaviors, is touchy or easily annoyed by others, is angry or resentful, and is spiteful and wants to get even. The set of symptom for ODD may be these eight symptom or any other set of symptoms.

At 120, indications of symptoms from the set of symptoms are received. The indications of symptoms are those symptoms that are exhibited by the patient. The indications of symptoms may be inputted by a patient, inputted by a clinician, received as a file, or may be received using any means of recording indications of symptoms.

For example, an indication can be received for each symptom of the set of symptoms associated with the disorder. The indication of the symptom can indicate the presence or absence of the symptom (e.g., that the patient does, or does not, exhibit the symptom), a level of severity or degree of the symptom (e.g., one of a range of severities), or another type of indication.

At 130, the probabilities of the indications of symptoms are calculated using the vectors for the set of symptoms. The probabilities may also be obtained by any method that derives the probability of symptoms given a disorder. For example, for each of the exhibited symptoms (e.g., the vectors indicating the presence or absence of a symptom), the vector values for a theta value may be multiplied to obtain a probability of the indications of symptoms for each theta value. Alternatively, instead of obtaining vectors and calculating the vectors, the probabilities may be directly received. The probabilities may be received by a file, inputted by a user, or another mean.

At 140, a posterior probability distribution of the disorder is calculated based on the computed probabilities of the indications of symptoms. The probability of the indications of symptoms, the probability of the disorder, and the likelihood of the indications of symptoms given the disorder may be obtained for each theta value, and used to calculate the posterior probability distribution of the disorder given the indication of symptoms. The probabilities may be obtained by, for example, the IRT method. The probabilities may also be obtained by other means and are not limited to the IRT method. For example, a clinician may obtain data from a study to derive the probabilities.

At 150, a PPOD Index for each theta value is computed from the posterior probability distribution. The PPOD Index may be calculated using a cumulative distribution function. For example, a posterior probability value may be obtained for each theta. However, since the posterior probability value is only for a particular theta, the posterior probability value does not factor other posterior probability values above that theta. Thus, a cumulative distribution function allows the posterior probability values for a particular theta value and posterior probability values above that value to be calculated, i.e., summed, to arrive at a PPOD Index for each theta value.

In any of the embodiments, the PPOD Index need not be calculated using a cumulative distribution function. For example, if a clinician was interested in a PPOD Index for specific theta values, that PPOD Index may also be calculated.

Whether the PPOD Index meets or exceeds a threshold for the disorder can be determined. For example, it can be determined whether the PPOD Index meets or exceeds the threshold for the disorder based on a theta value for the disorder. For ODD, the theta value is −0.38, so the PPOD Index for a theta value of −0.38 can be determined and used to determine how likely a patient suffers from ODD given the indication of symptoms.

The PPOD Index may include a lower bound and an upper bound for a given theta value. For example, instead of providing a single value for each theta, an upper and lower bound may be provided.

Because theta is a continuous score, it is practical to create a set of discrete variables (quadrature points) to approximate its possible range of values. For this reason, it is practical to report a lower bound and an upper bound for the PPOD Index by numerical integration the posterior distribution above the quadrature points closest to the diagnostic threshold. Alternatively, a lower bound and an upper bound can be estimate to represent confidence internals (e.g. 95% confidence interval).

Example 6

Example of Obtaining Vectors

Figure 2:
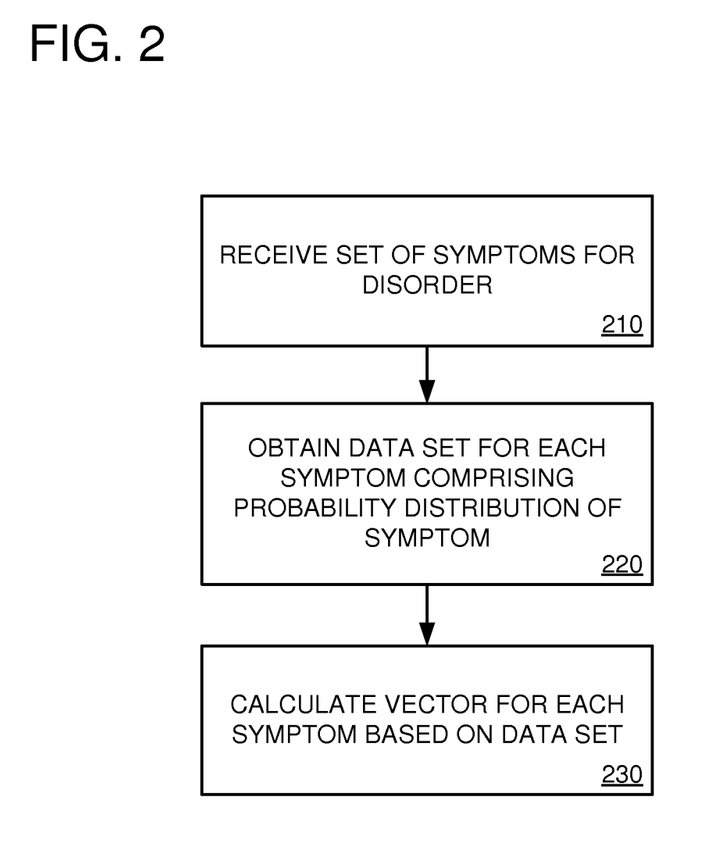
FIG. 2 is a flowchart of obtaining vectors in the exemplary method for diagnosing a disorder.

FIG. 2 is a flowchart of obtaining vectors in the exemplary method for diagnosing a disorder.

At 210, the set of symptoms for the disorder is received. The set of symptoms for the disorder may be received, for example, from the DSM.

At 220, a data set for each symptom is obtained. The data set may comprise a probability distribution of the symptom. The data set may be modeled using an IRT method. In any of the examples herein, the data set may be calculated or may be obtained from a file or another data source.

At 230, the vector for each symptom is calculated based on the data set. These vectors can be calculated using any one of several existing software programs (e.g., Item Response Theory for Patient-Reported Outcomes (IRTPRO), developed by Scientific Software International). Two vectors may be calculated for each symptom, representing the probability that the symptom is present (vector 1) or not present (vector 2)

given a particular discrete value of theta. Alternatively, only one vector or more than two vectors may be calculated for a symptom.

Example 7

Example of User Interface for Diagnosis Support Tool

Figure 3A:
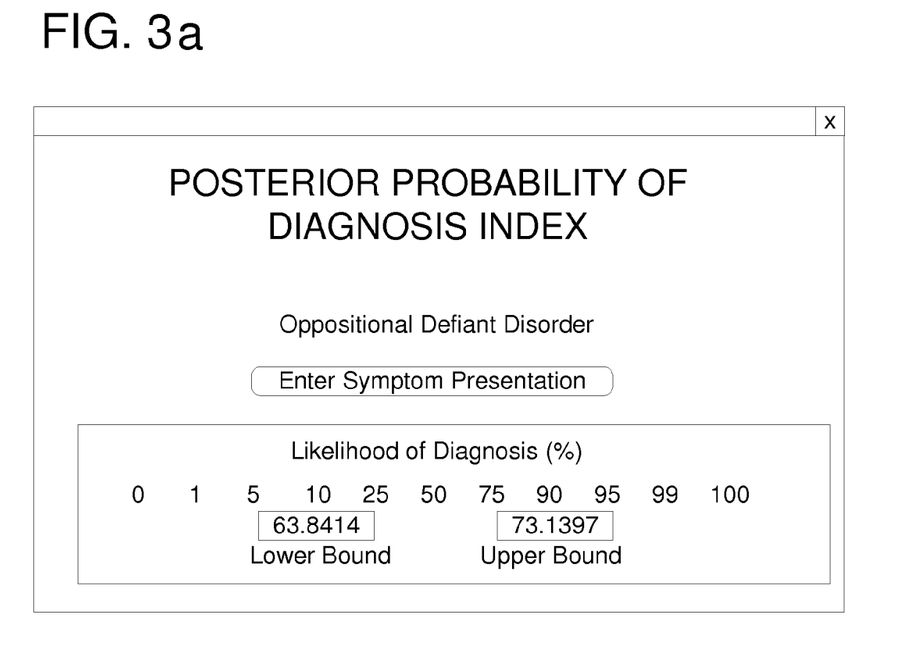
FIGS. 3a and 3b are exemplary screenshots of a diagnosis support tool.
Figure 3B:
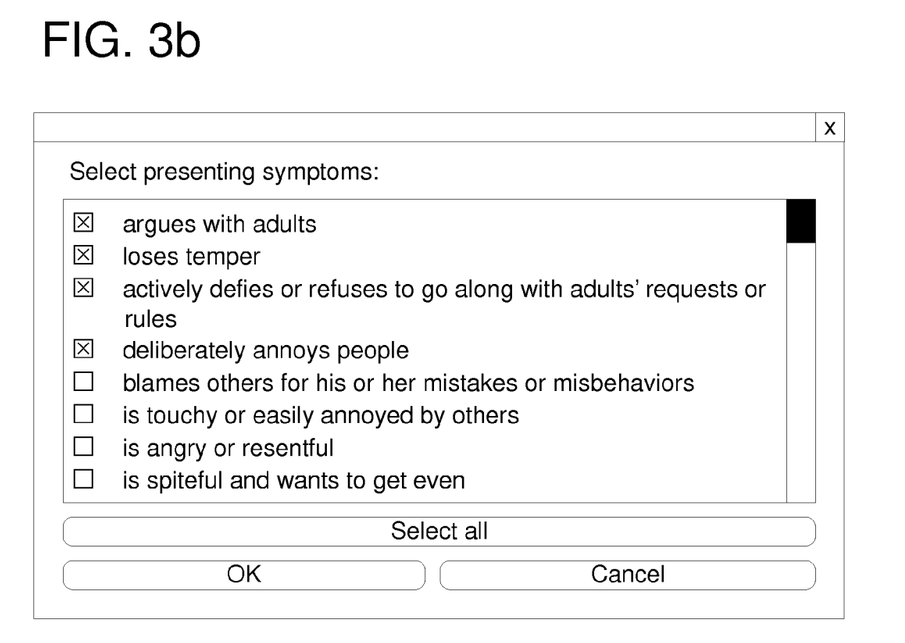
Figure 4:
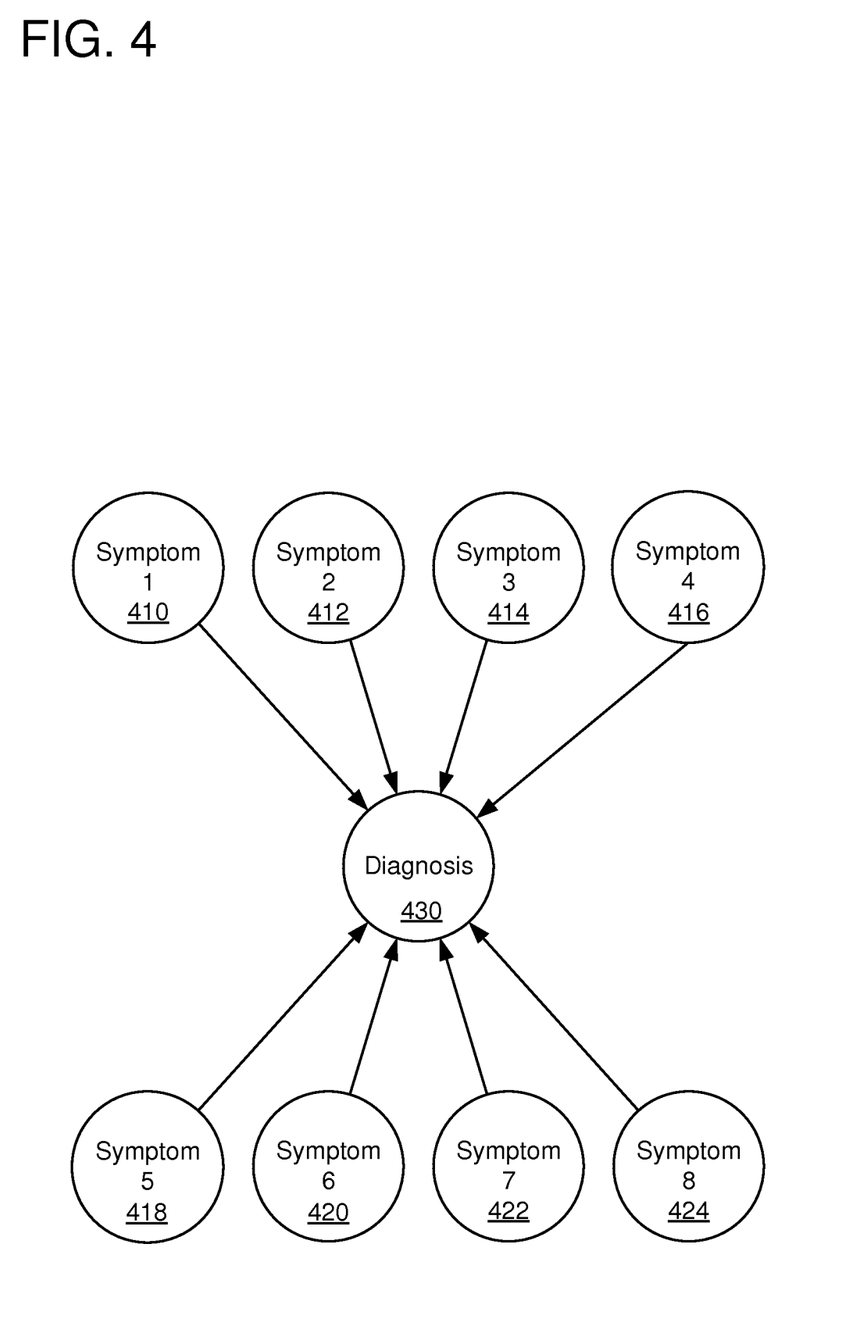
FIG. 4 is a diagram depicting a set of symptoms for a disorder.

FIGS. 3a and 3b are exemplary screenshots of a diagnosis support tool.

As shown in FIG. 3a, a PPOD Index may be provided, where the PPOD Index has an upper and lower bound. Although the upper and lower bound are presented as numeric values, the upper and lower bound can also be shown as points on a graph, a bar chart, or any other means of displaying upper and lower bounds. If the user wants to enter the symptoms that are present in the patient, a button may be provided.

As shown in FIG. 3b, the set of symptoms for the disorder may be presented to the user. The user may select one or more of the symptoms from the set of symptoms, and the probability of the one or more symptoms may be determined using any of the embodiments described herein. The PPOD Index may be computed using any of the embodiments described herein. After the user selects one or more symptoms and is finished with their selection, the user interface may return to the first screen and display the upper and lower bounds of the PPOD Index.

Example 8

Example Using Oppositional Defiant Disorder (ODD)

This section describes an example of applying the techniques described herein to ODD. A study was performed on a group of 321 subjects who were referred for services due to disruptive behavior.

Symptoms of ODD were assessed using the Vanderbilt Assessment Scale-Parent (VAS-Parent). Items 19 through 26 of the VAS-Parent correspond to the eight DSM symptoms of ODD: 19—argues with adults; 20—loses temper; 21—actively defies or refuses to go along with adults' requests or rules; 22—deliberately annoys people; 23—blames others for his or her mistakes or misbehaviors; 24—is touchy or easily annoyed by others; 25—is angry or resentful; and 26—is spiteful and wants to get even. Each item of the VAS-Parent was rated on 4-point Likert scale (0=Never; 1=Sometimes; 2=Often; 3=Very Often). To be consistent with DSM diagnostic criteria, each item was recoded as a "symptom" (1=Often or Very Often) or "not a symptom" (0=Never or Sometimes). Using this dichotomous variable, the Cronbach's alpha was high in the study (0.80). Factor analysis of the items supported a four-factor solution with the ODD and conduct disorder (CD) items loading onto a separate factor from the inattention, hyperactivity/impulsivity items, and the anxiety-depression items. In addition, scores on these items are significantly associated with the likelihood of being suspended from school and the likelihood of being referred to a mental health provider.

A single factor confirmatory model was fitted using the Mplus statistical program to check for unidimensionality. The indicators (items) were treated as categorical variables. The robust weighted least squares estimator was invoked. Criteria for fit indices were <0.08 for the root mean square error of approximation (RMSEA) and >0.90 for the comparative fit index (CFI) and the Tucker-Lewis index (TLI).

Data analysis was conducted using IRTPRO. The data was fit to a two-parameter logistic (2PL) IRT model for dichotomous items. Threshold parameters ($\beta$s) and discrimination parameters (as) were estimated for each of the eight ODD symptoms. Each patient's IRT trait level $\theta$ and standard error of $\theta$ were also estimated. Scoring was based on the expected a posteriori (EAP) estimation method and assuming a standard normal prior distribution.

The PPOD Index was defined as the likelihood that a patient meets or exceeds the threshold on the latent trait $\theta$ equivalent to the DSM criteria for ODD of four or more symptoms. This threshold was defined as the lowest $\theta$ out of all patients with four of more symptoms. In the current example, the $\theta$ threshold was −0.38. The PPOD Index was estimated using two different methods. The first method (Method A) used the estimates of $\theta$ and the standard error of $\theta$ for each patient from the IRTPRO output to estimate the likelihood that each patient met or exceed a latent trait $\theta$ of −0.38. A limitation of this method is the assumption that the posterior distribution of $\theta$ is normally distributed. To examine the potential bias resulting from this assumption, the PPOD Index was calculated using a second method. In the second method (Method B), numerical integration was used to integrate the posterior distribution of $\theta$ from −0.38 to 2.9 (the maximum quadrature point for IRTPRO). Because IRTPRO does not provide the density heights of the posterior distribution for each quadrature point for each pattern of responses, a program for the MATLAB computing environment was created to generate the probability masses for each of discrete values of $\theta$ for the posterior distribution for each response pattern that is inputted and estimate the PPOD Index using numerical integration:

```
%Posterior Probability of Diagnosis (PPOD) Index PROGRAM
Blames = input('BLAMES: ');
Argues = input('ARGUES: ');
Temper = input('TEMPER: ');
Defies = input('DEFIES: ');
Touchy = input('TOUCHY: ');
Annoys = input('ANNOYS: ');
Angry = input('ANGRY: ');
Spiteful = input('SPITEFUL: ');
%The following vectors (Blames0, Blames1, Argues0, Argues1, Temper0,
%Temper1, Defies0, Defies1, Touchy0, Touchy1, Annoys0, Annoys1,
Angry0,
%Angry1, Spiteful0, Spiteful1) are based on the output from IRTPRO.
if Blames==0
    A=Blames0;
else
    A=Blames1;
end
if Argues==0
    B=Argues0;
else
    B=Argues1;
end
if Temper==0
    C=Temper0;
else
    C=Temper1;
end
if Defies==0
    D=Defies0;
else
    D=Defies1;
end
if Touchy==0
    E=Touchy0;
else
    E=Touchy1;
end
if Annoys==0
    F=Annoys0;
```

-continued

```
else
    F=Annoys1;
end
if Angry==0
    G=Angry0;
else
    G=Angry1;
end
if Spiteful==0
    H=Spiteful0;
else
    H=Spiteful1;
end
P_ResponsePattern_given_Theta = A.*B.*C.*D.*E.*F.*G.*H;
% The vector Ptheta represents the density heights for the normal
distribution for
% 60 quadrature points (-3.0 to 2.9 in 0.1 increments).
P_ResponsePattern_given_Theta_TIMES_P_Theta =
P_ResponsePattern_given_Theta. *Ptheta;
P_ResponsePattern =
sum(P_ResponsePattern_given_Theta_TIMES_P_Theta);
%P_ResponsePattern is the NORMALIZING CONSTANT
P_Theta_given_ResponsePattern =
P_ResponsePattern_given_Theta_TIMES_P_Theta/
P_ResponsePattern;
Cumulative_sum_of_P_Theta_given_ResponsePattern =
cumsum(P_Theta_given_ResponsePattern);
PPOD = 1- Cumulative_sum_of_P_Theta_given_ResponsePattern ;
PPOD _Upper_Bound = PPOD(26,1);
PPOD _Lower_Bound = PPOD(27,1);
PPOD _Lower_Bound
PPOD _Upper_Bound
Commandwindow
```

Also, because IRTPRO uses 60 quadrature points ranging from −3.0 to 2.9 in increments of 0.1, quadrature points on either side of −0.38 were selected, Lower Bound (−0.30) and Upper Bound (−0.40).

Item frequencies (proportion endorsed) for the sample were as follow: "argues"=0.71, "temper"=0.72, "defies"=0.66, "annoys"=0.52, "blame"=0.71, "touchy"=0.54, "angry"=0.46, and spiteful"=0.29. Internal consistency for the eight items was good (Cronbach's alpha=0.80). Total symptom counts ranged from 0 to 8 (mean=4.6; standard deviation=2.5) and were symmetrical (skewness=−0.35; standard error=0.14) but platykurtic (excess kurtosis=−0.98; standard error=0.27).

Results from the one factor confirmatory factor analysis (CFA) supported a one factor solution. Although the chi-square test was significant, $\chi^2$ (16)=49.71, p=0.00, alternative fit indices indicated an adequate fit: CFI=0.96, TLI=0.97, and root mean square error of approximation (RMSEA)=0.08.

The item parameter estimates for the two-parameter (2PL) model are summarized in Table 1.

TABLE 1

| Item | Item Parameters | | Standard Errors | |
|---|---|---|---|---|
| | $\alpha$ | $\beta$ | $\sigma\alpha$ | $\sigma\beta$ |
| Argues with adults | 2.05 | −0.72 | 0.33 | 0.12 |
| Loses temper | 2.59 | −0.69 | 0.44 | 0.11 |
| Actively defies or refuses to go along with adults' requests or rules | 1.77 | −0.56 | 0.29 | 0.11 |
| Deliberately annoys people | 1.65 | −0.07 | 0.26 | 0.10 |
| Blames others for his or her mistakes or misbehaviors | 1.50 | −0.82 | 0.25 | 0.15 |
| Is touchy or easily annoyed by others | 1.61 | −0.16 | 0.26 | 0.11 |
| Is angry or resentful | 2.12 | 0.14 | 0.35 | 0.09 |
| Is spiteful and wants to get even | 2.29 | 0.68 | 0.43 | 0.11 |

In Table 1, for example, "blames others for his or her mistakes or misbehaviors" has the lowest threshold parameter ($\beta$=−0.82). A child would need to exceed this ODD trait level for there is a 50% chance that his or her parent would endorse this item as "often" or "very often". The item "is spiteful and wants to get even" has the highest threshold parameter ($\beta$=0.68). A child would need to have a much higher ODD trait level before his or her parent would have a 50% chance of endorsing this item as "often" or "very often." All eight ODD symptoms have good discrimination parameters (all a parameters above 1.0) and ranged from 1.50 ("blames others for his or her mistakes or misbehaviors") to 2.59 ("loses temper").

The IRT model fit was examined for each item using the IRTFIT macro program with an option specified to implement the sum score based method by Orlando and Thissen (see Orlando, M., & Thissen, D. (2003), Further investigation of the performance of S-$X^2$: An item fit index for use with dichotomous item response theory models, *Applied Psychological Measurement*, 27, 289-298), which uses the sum score instead of $\theta$ for computing the predicted and observed frequencies. The likelihood ratio G-square(S-$G^2$) and the Pearson's chi-square (S-$X^2$) fit statistics use the sum of score of all items and compare the predicted and observed response frequencies for each level of the sum score. Significance tests were calculated and plots were produced for each level of sum score. Table 2 shows the resulting S-$G^2$ and S-$X^2$ statistics. All items show good item fit using the 0.01 criteria.

TABLE 2

| Item | Label | df | S-$G^2$ | Prob S-$G^2$ | S-$X^2$ | Prob S-$X^2$ |
|---|---|---|---|---|---|---|
| 1 | Argues | 5 | 2.60 | 0.7618 | 2.56 | 0.7679 |
| 2 | Temper | 5 | 2.22 | 0.8174 | 2.22 | 0.8174 |
| 3 | Defies | 5 | 1.47 | 0.9165 | 1.48 | 0.9155 |
| 4 | Annoys | 6 | 1.86 | 0.9325 | 1.84 | 0.9337 |
| 5 | Blames | 6 | 14.25 | 0.0270 | 13.48 | 0.0361 |
| 6 | Touchy | 6 | 3.38 | 0.7595 | 3.38 | 0.7593 |
| 7 | Angry | 5 | 9.32 | 0.0969 | 9.51 | 0.0904 |
| 8 | Spiteful | 4 | 0.61 | 0.9618 | 0.61 | 0.9616 |

There were a total of 97 different response patterns in the example, out of 256 possible. Most of these response patterns (n=62) occurred just once or twice. A large proportion of the sample (40%; n=128) endorsed one of the nine perfectly consistent response patterns (e.g., 1,1,1,1,0,0,0,0).

Figure 5A:
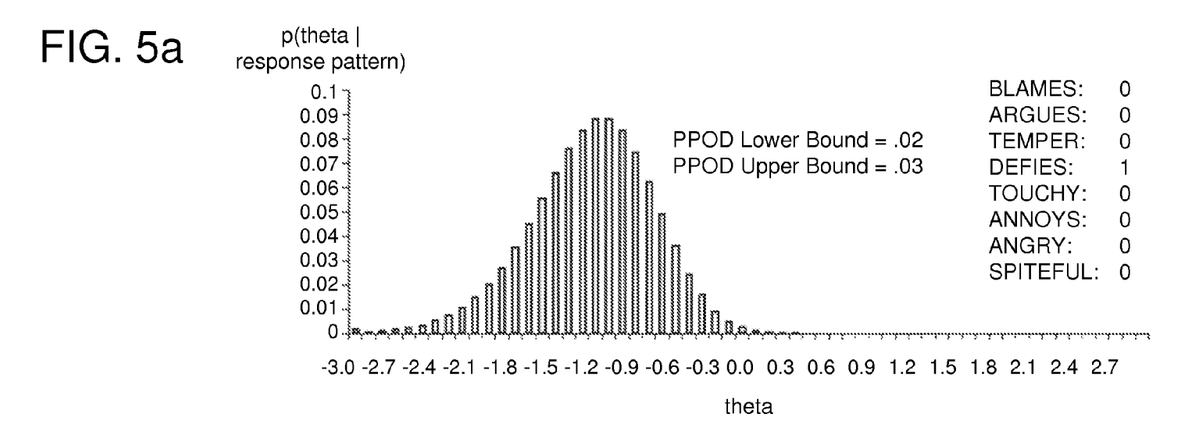
FIGS. 5a and 5b are exemplary charts depicting theta distributions.
Figure 5B:
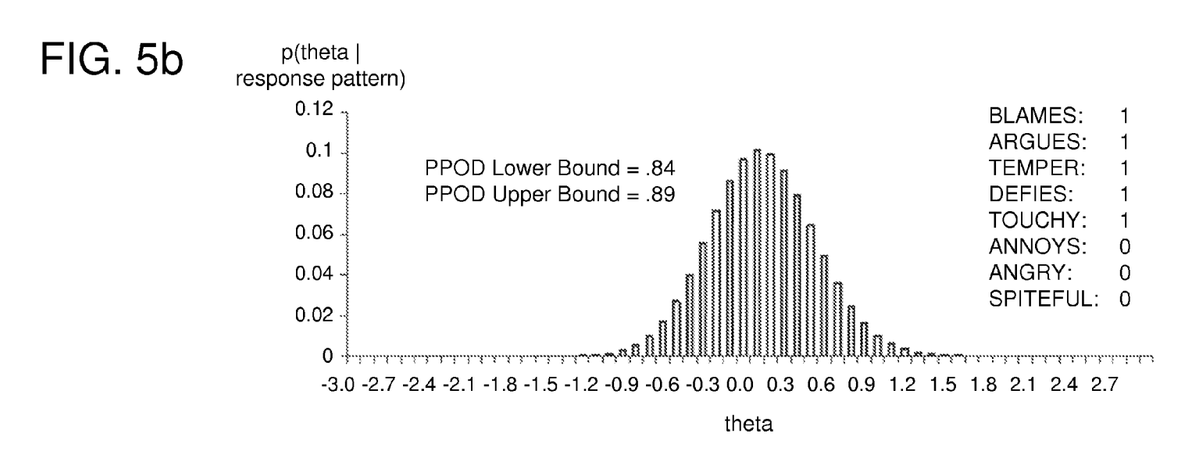

The two methods for estimating the PPOD Index yielded comparable estimates. Specifically, PPOD Indices estimated using Method A (standard normal cumulative distribution function) generally fell between the lower bound and the upper bound for the PPOD Index using Method B (numerical integration of the posterior distribution). FIGS. 5a and 5b shows examples of the posterior distribution of $\theta$ for two response patterns estimated using Method B. The graphs provide a visual aid in conceptualizing the PPOD Index, which is the sum of the probability masses (represented by bars) for $\theta$ values −0.30 to 2.9 (Lower Bound) and −0.40 to 2.9 (Upper Bound). Each response pattern (256 possible) has its own posterior distribution of $\theta$, although just two examples are shown in the figure.

Across patients, there was great variability in the PPOD Index, with values ranging from 0.01 (1% chance that the patient meets or exceeds the diagnostic threshold for ODD) to >0.99 (greater than 99% chance the patient meets or exceeds the diagnostic threshold for ODD). Table 3 summarizes the PPOD Index range associated with each symptoms count.

TABLE 3

| Symptom Count | DSM Diagnosis | θ Range | PPOD Index Range |
|---|---|---|---|
| 8 (n = 23) | YES | 1.373 | >.99 |
| 7 (n = 25) | YES | 0.662 to 1.318 | >.99 |
| 6 (n = 25) | YES | 0.230 to 0.555 | .93 to .98 |
| 5 (n = 30) | YES | −0.025 to 0.251 | .82 to .94 |
| 4 (n = 44) | YES | −0.376 to −0.037 | .50 to .81 |
| 3 (n = 39) | NO | −0.670 to −0.384 | .23 to .50 |
| 2 (n = 46) | NO | −0.965 to −0.679 | .08 to .21 |
| 1 (n = 45) | NO | −1.290 to −1.062 | .03 to .06 |
| 0 (n = 44) | NO | −1.693 | .01 |

Patients close to the DSM-IV (Diagnostic and Statistical Manual of Mental Disorders; 4th ed.) diagnostic threshold of 4 symptoms have the greatest degree of diagnostic uncertainty. Patients with a symptom count of four had PPOD Indices ranging from 0.50 to 0.81 depending on their individual response pattern of endorsed and not endorsed items.

Of the 218 patients who met the DSM criteria of ODD (four or more symptoms), the PPOD Index indicates a 95% confidence level for 132 of these diagnoses (61%). Similarly, of the 103 patients who did not meet the DSM criteria of ODD (three of fewer symptoms), the PPOD index indicates a 95% confidence level for 41 of these cases (40%). Overall, there was a 95% confidence level for 173 of the patients in this example (54%).

Using an IRT approach, the eight symptoms of ODD had different severity threshold parameters. In other words, varying levels of the latent trait are required before a parent has a 50% chance of endorsing the item as "often" or "very often." The item "blames others for his or her mistakes or misbehaviors" had the lowest threshold parameter and the item "is spiteful and wants to get even" had the highest threshold parameter. Although all eight items had good discriminability, some items were marginally better than others. "Loses temper" was found to have the highest discrimination parameter whereas "blames others for his or her mistakes or misbehaviors" had the lowest discrimination parameter. The good discriminability of all eight symptoms is consistent with other research findings for which IRT analyses have been applied to DSM criteria (i.e. symptoms).

Ninety-seven different response patterns were represented in the example, resulting in more variability in latent trait scores than traditional DSM symptom counts. Notably, patients with the same symptom count had different latent trait scores depending in individual response patterns of endorsed ODD symptoms. The results even illustrated that it is possible for a patient with fewer symptoms to have a higher latent trait score than a patient with more symptoms. In other words, which symptoms are endorsed may sometimes matter more than the total number of symptoms endorsed.

Using traditional DSM diagnostic criteria, a clinician is forced to make a categorical decision (diagnosis versus no diagnosis). This approach implies a degree of confidence in the diagnosis that might not be justified. The PPOD Index provides and alternative (and/or supplemental) method by which the clinician can convey the appropriate degree of certainty (or lack thereof) associated with a diagnosis. This is especially important when a patient is close to the diagnostic threshold and confidence in the diagnosis is low. A few of the patients in the example with symptom counts of four even had a PPOD index around 0.50. By DSM criteria, these patients would meet criteria of ODD, yet the confidence in the diagnoses would be equivalent to flipping a coin.

In the current example, the two methods for estimating the PPOD Index values yielded comparable results. However, Method A (standard normal cumulative distribution function) is a heuristic and should only be used if the posterior distribution of θ is close to a normal distribution. Therefore, Method A is only recommended to be used when there is no significant skewness of symptom counts in the sample dataset. Method B (numerical integration of the posterior distribution), although requiring additional analyses, does not require that the posterior distribution of θ be normally distributed. However, Method B provides only an approximation of PPOD Index values due to a finite number of quadrature points. Method B is recommended to be used when there is significant skewness of symptom counts in the sample dataset.

Tables 4 and 5 describe another implementation of the example using ODD. Table 4 shows vectors for 3 of the symptoms of ODD (argues with adults, loses temper, and actively defies or refuses to go along with adults' requests or rules), and Table 5 shows how the PPOD was calculated from the vectors. For Tables 4 and 5, only theta values for −3 to −2.6, −0.5 to −0.3, and 2.5-2.9 are shown for illustrative purposes.

TABLE 4

| theta (θ) | Argues0 | Argues1 | Temper0 | Temper1 | Defies0 | Defies1 | ... |
|---|---|---|---|---|---|---|---|
| −3 | 0.991 | 0.009 | 0.997 | 0.003 | 0.987 | 0.013 | |
| −2.9 | 0.989 | 0.011 | 0.997 | 0.003 | 0.984 | 0.016 | |
| −2.8 | 0.986 | 0.014 | 0.996 | 0.004 | 0.981 | 0.019 | |
| −2.7 | 0.983 | 0.017 | 0.995 | 0.005 | 0.978 | 0.022 | |
| −2.6 | 0.979 | 0.021 | 0.993 | 0.007 | 0.974 | 0.026 | |
| | | | ... | | | | |
| −0.5 | 0.389 | 0.611 | 0.376 | 0.624 | 0.474 | 0.526 | |
| −0.4 | 0.342 | 0.658 | 0.318 | 0.682 | 0.43 | 0.57 | |
| −0.3 | 0.297 | 0.703 | 0.264 | 0.736 | 0.388 | 0.612 | |
| | | | ... | | | | |
| 2.5 | 0.001 | 0.999 | 0 | 1 | 0.004 | 0.996 | |
| 2.6 | 0.001 | 0.999 | 0 | 1 | 0.004 | 0.996 | |
| 2.7 | 0.001 | 0.999 | 0 | 1 | 0.003 | 0.997 | |
| 2.8 | 0.001 | 0.999 | 0 | 1 | 0.003 | 0.997 | |
| 2.9 | 0.001 | 0.999 | 0 | 1 | 0.002 | 0.998 | |

TABLE 5

| theta (θ) | p(D\|θ) | p(θ) | p(D\|θ) * p(θ) | p(D) | p(θ\|D) | CDF | PPOD Index |
|---|---|---|---|---|---|---|---|
| −3 | 1.028E−10 | 0.0016 | 1.64407E−13 | 0.0167 | 9.695E−12 | 9.69454E−12 | 1 |
| −2.9 | 1.968E−10 | 0.0006 | 1.18077E−13 | 0.0167 | 6.963E−12 | 1.66572E−11 | 1 |
| −2.8 | 5.643E−10 | 0.0008 | 4.51469E−13 | 0.0167 | 2.662E−11 | 4.32789E−11 | 1 |
| −2.7 | 1.337E−09 | 0.001 | 1.3369E−12 | 0.0167 | 7.883E−11 | 1.22112E−10 | 1 |
| −2.6 | 3.641E−09 | 0.0014 | 5.09745E−12 | 0.0167 | 3.006E−10 | 4.22692E−10 | 1 |
| | | | ... | | | | |
| −0.5 | 1.928E−02 | 0.0352 | 0.000678575 | 0.0167 | 0.04001342 | 0.104105785 | 0.895894 |
| −0.4 | 2.552E−02 | 0.0368 | 0.000939212 | 0.0167 | 0.05538238 | 0.15948817 | 0.840512 |
| −0.3 | 3.182E−02 | 0.0381 | 0.001212278 | 0.0167 | 0.07148421 | 0.230972375 | 0.769028 |

TABLE 5-continued

| theta ($\theta$) | p(D\|$\theta$) | p($\theta$) | p(D\|$\theta$) * p($\theta$) | p(D) | p($\theta$\|D) | CDF | PPOD Index |
|---|---|---|---|---|---|---|---|
| ... | | | | | | | |
| 2.5 | 1.432E−06 | 0.0017 | 2.43454E−09 | 0.0167 | 1.436E−07 | 0.999999747 | 1.09E−07 |
| 2.6 | 7.036E−07 | 0.0014 | 9.84983E−10 | 0.0167 | 5.808E−08 | 0.999999891 | 5.11E−08 |
| 2.7 | 3.924E−07 | 0.001 | 3.92445E−10 | 0.0167 | 2.314E−08 | 0.999999949 | 2.80E−08 |
| 2.8 | 2.517E−07 | 0.0008 | 2.01337E−10 | 0.0167 | 1.187E−08 | 0.999999984 | 1.61E−08 |
| 2.9 | 1.242E−07 | 0.0022 | 2.73337E−10 | 0.0167 | 1.612E−08 | 1 | 0 |

In Table 4, the vectors for argues with adults, loses temper, and actively defies or refuses to go along with adults' requests or rules are shown. The total number of theta values was 60, so each vector has 60 values according to the theta values. In this example, vectors for the symptom being exhibited and not exhibited were calculated. Alternatively, only those vectors for a symptom being exhibited or vectors for a symptom not being exhibited may be calculated. Further, the vectors may be recalculated based on new information, such as the values of the vectors changing due to new symptoms or new information.

Table 5, shows the calculations for the PPOD Index using the vectors. In Table 5, theta ($\theta$), the probability of theta (p($\theta$)) and the probability of the disorder (p(D)) may be obtained from a data set. However, theta ($\theta$), the probability of theta (p($\theta$)) and the probability of the response pattern (p(D)) need not be obtained from a data set, and may be obtained by, e.g., live data, default values, etc.

The likelihood of the response pattern given theta (p(D|$\theta$)) may be calculated from the vectors, where the values are computed based on the symptom being exhibited or not exhibited. For example, using Table 4, if the patient argues with adults and loses their temper, but does not actively defy or refuse to go along with adults' requests or rules, for a theta of −3, 0.991, 0.997, and 0.013 would be used as the vector values. For the remaining symptoms, the values depending on whether the symptom is exhibited or not are also used to compute the likelihood of the response pattern given theta (p(D|$\theta$)).

The values for p(D|$\theta$)*p($\theta$) can be computed from the likelihood of the response pattern given theta (p(D|$\theta$)) and the probability of theta (p($\theta$)) for each theta value. For example, using Table 5, for a theta of −3, p(D|$\theta$)*p($\theta$)=1.028× $10^{-10}$*0.0016=1.64407×$10^{-13}$.

The values for the likelihood of theta given the response pattern for p($\theta$|D) can be obtained using Equation 1 above. Thus, for a theta of −3, p($\theta$|D)=1.64407×$10^{-13}$/0.0167=9.695×$10^{-12}$. Using a cumulative distribution function (CDF), the PPOD index can be computed for each theta. For example, using a theta of −2.9, the CDF is the p($\theta$|D) for a theta of −2.9+ the CDF for a theta of −3 (i.e., 6.963×$10^{-12}$+9.695×$10^{-12}$). The PPOD Index is 1—the CDF.

Example 9

Exemplary Computing Environment

Figure 6:
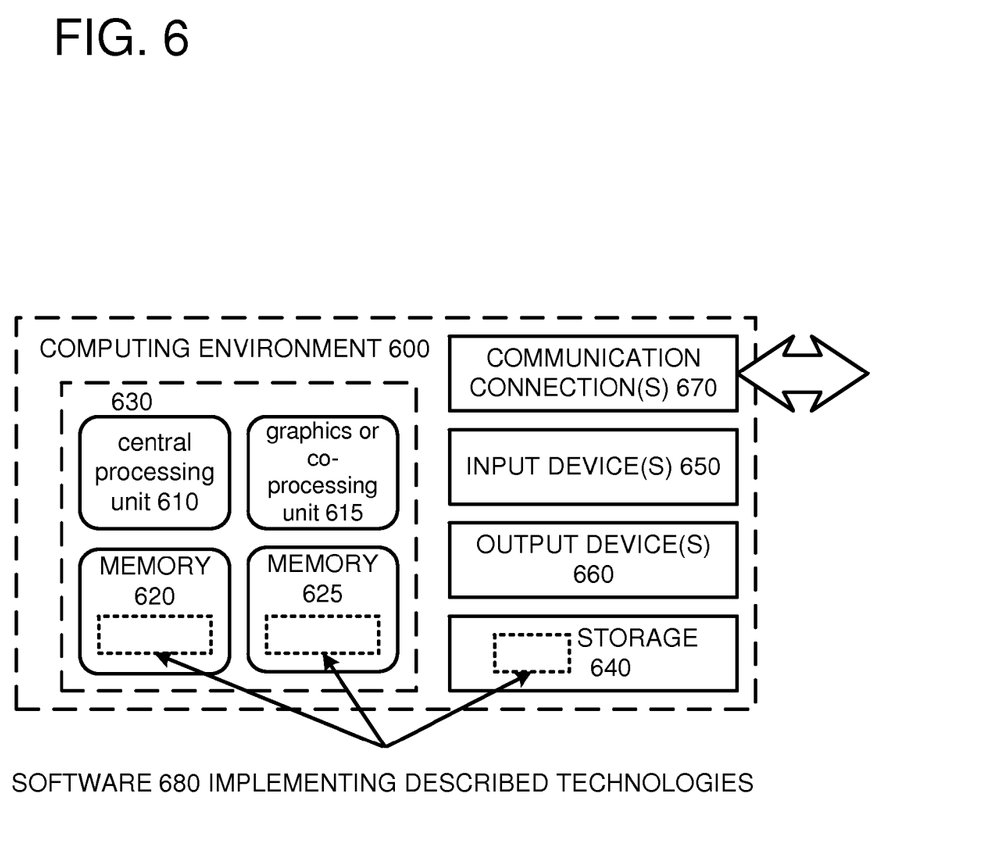
FIG. 6 is a diagram of an exemplary computing system in which some described embodiments can be implemented.

FIG. 6 depicts a generalized example of a suitable computing environment 600 in which the described innovations may be implemented. The computing environment 600 is not intended to suggest any limitation as to scope of use or functionality, as the innovations may be implemented in diverse general-purpose or special-purpose computing systems. For example, the computing environment 600 can be any of a variety of computing devices (e.g., desktop computer, laptop computer, server computer, tablet computer, media player, gaming system, mobile device, etc.).

With reference to FIG. 6, the computing environment 600 includes one or more processing units 610, 615 and memory 620, 625. In FIG. 6, this basic configuration 630 is included within a dashed line. The processing units 610, 615 execute computer-executable instructions. A processing unit can be a general-purpose central processing unit (CPU), processor in an application-specific integrated circuit (ASIC) or any other type of processor. In a multi-processing system, multiple processing units execute computer-executable instructions to increase processing power. For example, FIG. 6 shows a central processing unit 610 as well as a graphics processing unit or co-processing unit 615. The tangible memory 620, 625 may be volatile memory (e.g., registers, cache, RAM), non-volatile memory (e.g., ROM, EEPROM, flash memory, etc.), or some combination of the two, accessible by the processing unit(s). The memory 620, 625 stores software 680 implementing one or more innovations described herein, in the form of computer-executable instructions suitable for execution by the processing unit(s).

A computing system may have additional features. For example, the computing system 600 includes storage 640, one or more input devices 650, one or more output devices 660, and one or more communication connections 670. An interconnection mechanism (not shown) such as a bus, controller, or network interconnects the components of the computing system 600. Typically, operating system software (not shown) provides an operating environment for other software executing in the computing system 600, and coordinates activities of the components of the computing system 600.

The tangible storage 640 may be removable or non-removable, and includes magnetic disks, magnetic tapes or cassettes, CD-ROMs, DVDs, or any other medium which can be used to store information in a non-transitory way and which can be accessed within the computing system 600. The storage 640 stores instructions for the software 680 implementing one or more innovations described herein.

The input device(s) 650 may be a touch input device such as a keyboard, mouse, pen, or trackball, a voice input device, a scanning device, or another device that provides input to the computing system 600. For video encoding, the input device(s) 650 may be a camera, video card, TV tuner card, or similar device that accepts video input in analog or digital form, or a CD-ROM or CD-RW that reads video samples into the computing system 600. The output device(s) 660 may be a display, printer, speaker, CD-writer, or another device that provides output from the computing system 600.

The communication connection(s) 670 enable communication over a communication medium to another computing entity. The communication medium conveys information such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

The innovations can be described in the general context of computer-executable instructions, such as those included in program modules, being executed in a computing system on a target real or virtual processor. Generally, program modules include routines, programs, libraries, objects, classes, components, data structures, etc. that perform particular tasks or implement particular abstract data types. The functionality of the program modules may be combined or split between program modules as desired in various embodiments. Computer-executable instructions for program modules may be executed within a local or distributed computing system.

The terms "system" and "device" are used interchangeably herein. Unless the context clearly indicates otherwise, neither term implies any limitation on a type of computing system or computing device. In general, a computing system or computing device can be local or distributed, and can include any combination of special-purpose hardware and/or general-purpose hardware with software implementing the functionality described herein.

Example 10

Exemplary Cloud Computing Environment

Figure 7:
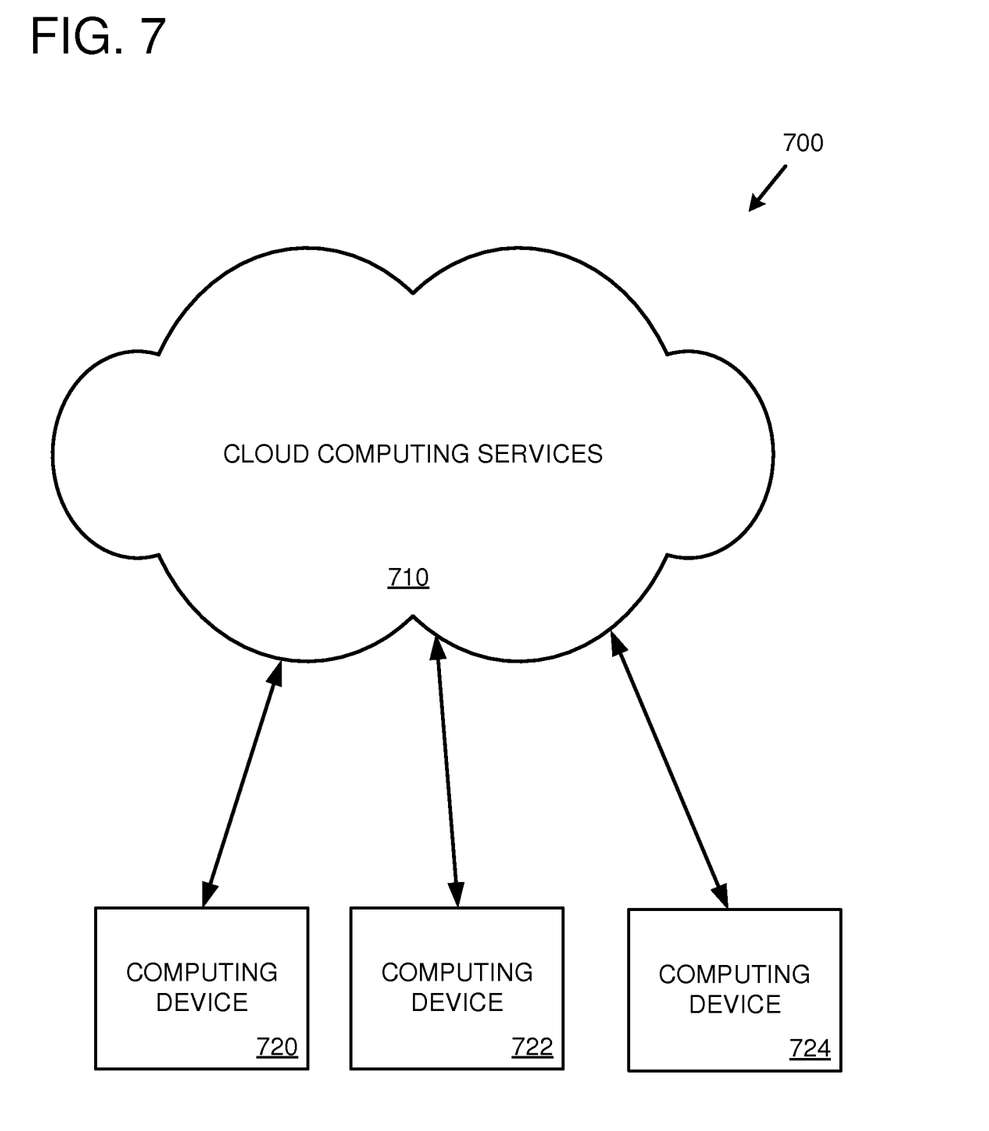
FIG. 7 is an exemplary cloud computing environment that can be used in conjunction with the technologies described herein.

FIG. 7 depicts an example cloud computing environment 700 in which the described technologies can be implemented. The cloud computing environment 700 comprises cloud computing services 710. The cloud computing services 710 can comprise various types of cloud computing resources, such as computer servers, data storage repositories, networking resources, etc. The cloud computing services 710 can be centrally located (e.g., provided by a data center of a business or organization) or distributed (e.g., provided by various computing resources located at different locations, such as different data centers and/or located in different cities or countries).

The cloud computing services 710 are utilized by various types of computing devices (e.g., client computing devices), such as computing devices 720, 722, and 724. For example, the computing devices (e.g., 720, 722, and 724) can be computers (e.g., desktop or laptop computers), mobile devices (e.g., tablet computers or smart phones), or other types of computing devices. For example, the computing devices (e.g., 720, 722, and 724) can utilize the cloud computing services 710 to perform computing operators (e.g., data processing, data storage, and the like).

Example 11

Exemplary Implementations

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods.

Any of the disclosed methods can be implemented as computer-executable instructions stored on one or more computer-readable storage media and executed on a computing device (e.g., any available computing device, including smart phones or other mobile devices that include computing hardware). Computer-readable storage media are any available tangible media that can be accessed within a computing environment (e.g., non-transitory computer-readable media, such as one or more optical media discs, volatile memory components (such as DRAM or SRAM), or nonvolatile memory components (such as flash memory or hard drives)). By way of example and with reference to FIG. 6, computer-readable storage media include memory 620 and 625, and storage 640. The term computer-readable storage media does not include communication connections (e.g., 670) such as signals and carrier waves.

Any of the computer-executable instructions for implementing the disclosed techniques as well as any data created and used during implementation of the disclosed embodiments can be stored on one or more computer-readable storage media. The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C++, Java, Perl, JavaScript, Adobe Flash, or any other suitable programming language. Likewise, the disclosed technology is not limited to any particular computer or type of hardware. Certain details of suitable computers and hardware are well known and need not be set forth in detail in this disclosure.

It should also be well understood that any functionality described herein can be performed, at least in part, by one or more hardware logic components, instead of software. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

Furthermore, any of the software-based embodiments (comprising, for example, computer-executable instructions for causing a computer to perform any of the disclosed methods) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

The disclosed methods, apparatus, and systems should not be construed as limiting in any way. Instead, the present disclosure is directed toward all novel and nonobvious features and aspects of the various disclosed embodiments, alone and in various combinations and sub combinations with one another. The disclosed methods, apparatus, and systems are not limited to any specific aspect or feature or combination thereof, nor do the disclosed embodiments require that any one or more specific advantages be present or problems be solved.

Alternatives

The technologies from any example can be combined with the technologies described in any one or more of the other examples. In view of the many possible embodiments to which the principles of the disclosed technology may be applied, it should be recognized that the illustrated embodiments are examples of the disclosed technology and should not be taken as a limitation on the scope of the disclosed technology. Rather, the scope of the disclosed technology includes what is covered by the following claims. I therefore claim as my invention all that comes within the scope of these claims.

What is claimed is:

1. A method, implemented at least in part by one or more computing devices, for diagnosing a disorder, the method comprising:
    obtaining vectors for a set of symptoms associated with a disorder, wherein the vectors represents probability distributions for ranges of discrete theta values for the set of symptoms;
    receiving indications of symptoms from the set of symptoms;
    computing probabilities of the indications of symptoms using the vectors, wherein the probabilities are scaled by theta value;
    computing a posterior probability distribution of the disorder based on the computed probabilities of the indications of symptoms;
    computing a posterior probability of diagnosis index for each theta value from the posterior probability distribution, wherein the posterior probability of diagnosis index is at least one numerical value for each theta value indicating a probability of having the disorder; and
    determining whether the posterior probability of diagnosis index meets or exceeds a threshold for the disorder, wherein determining whether the posterior probability of diagnosis index meets or exceeds the threshold for the disorder is based on a theta value for the disorder.

2. The method of claim 1, wherein the obtaining vectors comprises:
    receiving the set of symptoms for the disorder;
    obtaining a data set for each symptom, wherein the data set comprises a probability distribution of the symptom; and
    calculating the vector for each symptom based on the data set.

3. The method of claim 2, wherein the data set is modeled using item response theory (IRT).

4. The method of claim 1, wherein the receiving indications of symptoms from the set of symptoms comprises:
    for each symptom of the set of symptoms:
        receiving an indication that indicates presence or absence of the symptom.

5. The method of claim 1, wherein the receiving indications of symptoms from the set of symptoms comprises:
    for each symptom of the set of symptoms:
        receiving an indication that indicates a degree of the symptom.

6. The method of claim 1, wherein the computing a posterior probability of diagnosis index for each theta value uses a cumulative distribution function.

7. The method of claim 1, wherein the posterior probability of diagnosis index comprises a lower bound and an upper bound for a given theta value.

8. The method of claim 1, wherein the disorder is oppositional defiant disorder, and wherein the set of symptoms comprises one or more of: argues with adults, loses temper, actively defies or refuses to go along with adults' requests or rules, deliberately annoys people, blames others for his or her mistakes or misbehaviors, is touchy or easily annoyed by others, is angry or resentful, and is spiteful and wants to get even.

9. The method of claim 1, wherein the indications of symptoms are for a patient, and wherein the method further comprises:
    displaying the posterior probability of diagnosis index for a theta value corresponding to the disorder, where the posterior probability of diagnosis index comprises an upper and lower bound.

10. A non-transitory computer-readable storage medium storing computer-executable instructions for causing a processor programmed thereby to perform a method comprising:
    obtaining vectors for a set of symptoms of a disorder, wherein the vectors represents probability distributions for ranges of discrete theta values for the set of symptoms;
    obtaining indications of symptoms from the set of symptoms;
    determining probabilities of the indications of symptoms using the vectors, wherein the probabilities are scaled by theta value;
    computing a posterior probability distribution of the disorder based on the determined probabilities of the indications of symptoms;
    computing a posterior probability of diagnosis index for each theta value from the posterior probability distribution using a cumulative distribution function, wherein the posterior probability of diagnosis index is at least one numerical value for each theta value indicating a probability of having the disorder; and
    determining whether the posterior probability of diagnosis index meets or exceeds a threshold for the disorder, wherein determining whether the posterior probability of diagnosis index meets or exceeds the threshold for the disorder is based on a theta value for the disorder.

11. The computer-readable storage medium of claim 10, wherein the obtaining vectors comprises:
    obtaining the set of symptoms for the disorder;
    obtaining a data set for each symptom, wherein the data set comprises a probability distribution of the symptom; and
    calculating the vector for each symptom based on the data set.

12. The computer-readable storage medium of claim 11, wherein the data set is modeled using item response theory (IRT).

13. A computing device comprising:
    a processing unit; and
    memory;
    the computing device configured to perform operations for diagnosing a disorder, the operations comprising:
        selecting one or more symptoms from a set of symptoms of a disorder;
        determining probabilities of the one or more symptoms, wherein the probabilities are scaled by theta value;
        computing a posterior probability distribution of the disorder based on the determined probabilities of the one or more of symptoms;

computing a posterior probability of diagnosis index for each theta value from the posterior probability distribution using a cumulative distribution function, the posterior probability of diagnosis index comprising an upper bound and a lower bound, wherein the posterior probability of diagnosis index is the upper bound and the lower bound for each theta value indicating a probability of having the disorder;

determining whether the posterior probability of diagnosis index meets or exceeds a threshold for the disorder, wherein determining whether the posterior probability of diagnosis index meets or exceeds the threshold for the disorder is based on a theta value for the disorder; and displaying the upper bound and lower bound.

14. The device of claim 13, the method further comprising:

selecting a disorder from a set of disorders; and obtaining vectors for the selected disorder, wherein the vectors are used to determine the probabilities of the one or more symptoms.

\* \* \* \* \*